US008377956B2

(12) United States Patent
Wun et al.

(10) Patent No.: US 8,377,956 B2
(45) Date of Patent: Feb. 19, 2013

(54) USE OF (3R)-4-{[(1S)-2-METHYL-1-(2-METHYLPROPANOYLOXY)PROPOXY]CARBONYLAMINO}-3-(4-CHLOROPHENYL)BUTANOIC ACID FOR TREATING URINARY INCONTINENCE

(75) Inventors: Aetna W. Wun, Basel (CH); David J. Wustrow, Saratoga, CA (US)

(73) Assignee: XenoPort, Inc., Santa Clara, CA (US)

( * ) Notice: Subject to any disclaimer, the term of this patent is extended or adjusted under 35 U.S.C. 154(b) by 167 days.

(21) Appl. No.: 13/037,541

(22) Filed: Mar. 1, 2011

(65) Prior Publication Data
US 2011/0212984 A1 Sep. 1, 2011

Related U.S. Application Data

(60) Provisional application No. 61/309,336, filed on Mar. 1, 2010.

(51) Int. Cl.
*A61K 31/27* (2006.01)
(52) U.S. Cl. .................. 514/278; 514/487; 514/305
(58) Field of Classification Search .................. 514/278, 514/487, 305
See application file for complete search history.

(56) References Cited

U.S. PATENT DOCUMENTS

| | | | |
|---|---|---|---|
| 5,698,155 | A | 12/1997 | Grosswald et al. |
| 7,109,239 | B2 | 9/2006 | Gallop et al. |
| 7,227,028 | B2 | 6/2007 | Gallop et al. |
| 7,300,131 | B2 | 11/2007 | Sabagami et al. |
| 7,300,956 | B2 | 11/2007 | Gallop et al. |
| 7,572,830 | B2 * | 8/2009 | Gallop et al. ............... 514/533 |
| 2008/0206332 | A1 | 8/2008 | Kidney et al. |
| 2009/0041806 | A1 | 2/2009 | Cundy |
| 2009/0118365 | A1 | 5/2009 | Benson et al. |
| 2009/0192325 | A1 | 7/2009 | Gallop et al. |
| 2009/0197958 | A1 | 8/2009 | Sastry et al. |
| 2009/0234138 | A1 | 9/2009 | Gallop et al. |
| 2010/0081830 | A1 | 4/2010 | Raillard et al. |
| 2010/0087667 | A1 | 4/2010 | Raillard et al. |
| 2010/0255093 | A1 | 10/2010 | Edgren et al. |

FOREIGN PATENT DOCUMENTS

| | | |
|---|---|---|
| EP | 1 721 607 A1 | 11/2006 |
| WO | WO 00/76490 A2 | 12/2000 |
| WO | WO 2004/064821 A1 | 8/2004 |
| WO | WO 2004/096141 A2 | 11/2004 |
| WO | WO 2005/025562 A1 | 3/2005 |
| WO | WO 2009/094569 A2 | 7/2009 |
| WO | WO 2009/096985 A1 | 8/2009 |
| WO | WO 2010/017504 A1 | 2/2010 |
| WO | WO 2010/102071 A1 | 9/2010 |

OTHER PUBLICATIONS

Abrams et al., "The Standardisation of Terminology of Lower Urinary Tract Function: Report From the Standardisation Sub-committee of the International Continence Society", *Neurol. and Urodynam.* (2002), 21: pp. 167-178.
Abrams, "Describing Bladder Storage Function: Overactive Bladder Syndrome and Detrusor Overactivity", *Urology* (2003), 62 (Supp. 5B): pp. 28-37.
Andersson, "The Overactive Bladder: Pharmacologic Basis of Drug Treatment", *Urology* (1997), 50(Supp. 6A): pp. 74-84.
Bowery, "$GABA_B$ receptors and their significance in mammalian pharmacology", *Trends Pharmacol. Sci.* (1989), 10: pp. 401-407.
Colli et al., "Overactive bladder treatments in early phase clinical trials", *Expert Opin Investig Drugs* (2007), 16(7): pp. 999-1007.
Hijaz et al., "Animal models of female stress urinary incontinence," *J Urology* (2008), 179: pp. 2103-2110.
Igawa et al., "Effects of GABA receptor stimulation and blockade on micturition in normal rats and rats with bladder outflow obstruction," *J Urology* (1993), 150: pp. 537-542.
Lal et al., "Arbaclofen Placarbil, A Novel R-Baclofen Prodrug: Improved Absorption, Distribution, Metabolism, and Elimination Properties Compared With R-Baclofen", *J Pharmacol Experimental Therapeutics* (2009), 330(3), 911-921.
Lam et al., "Pharmacologic management of overactive bladder," *Clin. Intervent. Aging* (2007), 2(3): pp. 337-345.
Misgeld et al., "A Physiological Role for $GABA_B$ Receptors and the Effects of Baclofen in the Mammalian Central Nervous System", *Prog. Neurobiol.* (1995), 46: pp. 423-462.
Ouslander, "Management of Overactive Bladder", *N Engl J Med* (2004), 350: pp. 786-799.
Pehrson et al., "Effects of γ-aminobutyrate B receptor modulation on normal micturition and oxyhemoglobin induced detrusor overactivity in female rats," *J Urology* (2002), 168: pp. 2700-2705.
Robinson et al., "New Drug Treatments for Urinary Incontinence", *Maturitas* (2010), 65: pp. 340-347.
Santicioli et al., "GABAB receptor mediated inhibition of field stimulation-induced contractions of rabbit bladder muscle in-vitro," *J Pharm Pharmacol* (1984), 36: pp. 378-381.
Taylor et al., "A Double-Blind Crossover Trial of Baclofen—a New Treatment for the Unstable Bladder Syndrome", *British J Urology* (1979), 51: pp. 504-505.
Tyagi et al., "$\beta_3$—Adrenoceptor Agonists for the Treatment of Overactive Bladder", *Drugs of the Future* (2009), 34(8): pp. 635-640.
Wein et al., "Definition and Epidemiology of Overactive Bladder", *Urology* (2002), 60(Supp. 5A): pp. 7-12.

* cited by examiner

*Primary Examiner* — Rei-tsang Shiao
(74) *Attorney, Agent, or Firm* — Dorsey & Whitney LLP

(57) ABSTRACT

Use of (3R)-4-{[(1S)-2-methyl-1-(2-methylpropanoyloxy)propoxy]carbonylamino}-3-(4-chlorophenyl)butanoic acid for treating urinary incontinence is disclosed.

20 Claims, No Drawings

USE OF (3R)-4-{[(1S)-2-METHYL-1-(2-METHYLPROPANOYLOXY)PROPOXY] CARBONYLAMINO}-3-(4-CHLOROPHENYL) BUTANOIC ACID FOR TREATING URINARY INCONTINENCE

CROSS-REFERENCE TO RELATED APPLICATIONS

This application claims the benefit under 35 U.S.C. §119 (e) from U.S. Provisional Application Ser. No. 61/309,336, filed Mar. 1, 2010, which is herein incorporated by reference in its entirety.

FIELD

This disclosure relates to the use of (3R)-4- {[(1S)-2-methyl-1-(2-methylpropanoyloxy)propoxy]carbonylamino}-3-(4-chlorophenyl)butanoic acid for treating urinary incontinence.

BACKGROUND

Urinary incontinence is any involuntary leakage of urine and can be categorized into five types based on the pattern of symptoms including urge incontinence, stress incontinence, overflow incontinence, functional incontinence, and mixed incontinence. Current pharmacological management of urinary incontinence includes muscarinic receptor antagonists such as oxybutynin, tolterodine, trospium, solifenacin, and darifenacin. Lam and Hilas, *Clinical Interventions in Aging* (2007), 2(3), 337-345. However, these anticholinergic drugs are contraindicated in patients with urinary retention, gastric retention, or uncontrolled narrow-angle glaucoma, and have possible anticholinergic side effects such as heat prostration, dry mouth, constipation, dry eyes, urinary retention, dizziness and blurred vision.

(±)-4-Amino-3-(4-chlorophenyl)butanoic acid (baclofen) is an analog of gamma-aminobutyric acid (i.e., GABA) that selectively activates $GABA_B$ receptors, resulting in neuronal hyperpolarization. $GABA_B$ receptors are located in laminae I-IV of the spinal cord, where primary sensory fibers end. These G-protein coupled receptors activate conductance by $K^+$-selective ion channels and can reduce currents mediated by $Ca^{2+}$ channels in certain neurons. Baclofen has a presynaptic inhibitory effect on the release of excitatory neurotransmitters and also acts postsynaptically to decrease motor neuron firing. Bowery, *Trends Pharmacol. Sci.* (1989), 10, 401-407: and Misgeld et al., *Prog. Neurobiol.* (1995), 46, 423-462. In a double blind crossover trial baclofen administered at a dose of 5 mg four times per day was shown to significantly improve diurnal and nocturnal of frequency of micturition and the severity of incontinence in patients with unstable bladder syndrome. Taylor and Bates, *British J Urology* (1979), 51, 504-505.

Recently, prodrugs of (R)-baclofen that are well absorbed in the large intestine/colon, and hence suitable for oral sustained release formulations, have been developed. Gallop et al., U.S. Pat. Nos. 7,109,239, 7,227,028, 7,300,131, and 7,572,830; Leung et al., US 2008/0206332: Cundy, US 2009/0041806: and Sastry et al., US 2009/0197958: each of which is incorporated by reference herein in its entirety. For example, (3R)-4-{[(1S)-2-methyl-1-(2-methylpropanoyloxy)propoxy]carbonylamino}-3-(4-chlorophenyl)butanoic acid, (1),

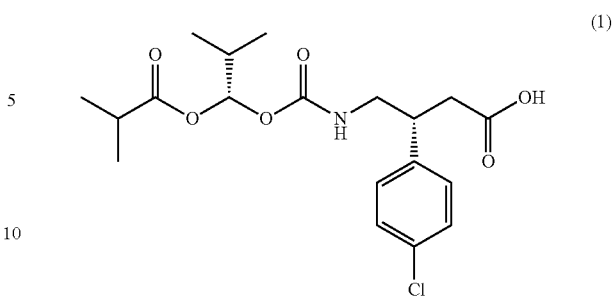

a prodrug of (R)-baclofen, exhibits high bioavailability as (R)-baclofen when dosed either orally or directly into the colon of a mammal. Gallop et al., U.S. Pat. No. 7,109,239: and Lal et al., *J Pharmacol Experimental Therapeutics* (2009), 330(3), 911-921.

SUMMARY

Use of (3R)-4-{[(1S)-2-methyl-1-(2-methylpropanoyloxy)propoxy]carbonylamino}-3-(4-chlorophenyl)butanoic acid for the treatment of urinary incontinence is disclosed. This use is expected to lead to enhanced therapeutic efficacy, provide higher plasma concentrations, reduce adverse side effects, and/or lower dosing frequency than treatment of urinary incontinence using only (R)-baclofen.

In a first aspect, methods of treating urinary incontinence in a patient are provided, the methods comprising administering to a patient in need of such treatment (3R)-4-{[(1S)-2-methyl-1-(2-methylpropanoyloxy)propoxy]carbonylamino}-3-(4-chlorophenyl)butanoic acid or a pharmaceutically acceptable salt thereof.

In a second aspect, methods of treating urinary incontinence in a patient are provided, the methods comprising administering to a patient in need of such treatment a pharmaceutical composition comprising (3R)-4-{[(1S)-2-methyl-1-(2-methylpropanoyloxy)propoxy]carbonylamino}-3-(4-chlorophenyl)butanoic acid and a pharmaceutically acceptable vehicle.

DETAILED DESCRIPTION

Definitions

Unless otherwise apparent from the context of use, "(3R)-4-{[(1S)-2-methyl-1-(2-methylpropanoyloxy)propoxy]carbonylamino}-3-(4-chlorophenyl)butanoic acid" refers to (3R)-4-{[(1S)-2-methyl-1-(2-methylpropanoyloxy)propoxy]carbonylamino}-3-(4-chlorophenyl) butanoic acid, a pharmaceutically acceptable salt thereof, a pharmaceutically acceptable solvate of any of the foregoing, and a crystalline form of any of the foregoing.

"Disease" refers to a disease, disorder, condition, or symptom of any of the foregoing.

"Patient" refers to a mammal, for example, a human.

"Pharmaceutically acceptable" refers to approved or approvable by a regulatory agency of the Federal government or of a state government, or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt. The term "pharmaceutically acceptable salt" includes hydrates and other solvates, as well as salts in crystalline or non-crystalline form.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which (3R)-4-{[(1S)-2-methyl-1-(2-methylpropanoyloxy)propoxy]carbonylamino}-3-(4-chlorophenyl)butanoic acid may be administered to a patient and which does not destroy the pharmacological activity thereof, and which is non-toxic when administered in doses sufficient to provide a therapeutically effective amount of (3R)-4-{[(1S)-2-methyl-1-(2-methylpropanoyloxy)propoxy]carbonylamino}-3-(4-chlorophenyl)butanoic acid.

"Pharmaceutical composition" refers to (3R)-4-{[(1S)-2-methyl-1-(2-methylpropanoyloxy)propoxy]carbonylamino}-3-(4-chlorophenyl)butanoic acid and at least one pharmaceutically acceptable vehicle, with which the (3R)-4-{[(1S)-2-methyl-1-(2-methylpropanoyloxy)propoxy]carbonylamino}-3-(4-chlorophenyl)butanoic acid is administered to a patient.

"Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecules is water.

"Treating" or "treatment" of urinary incontinence refers to reversing, alleviating, arresting, or ameliorating urinary incontinence or at least one of the clinical symptoms of urinary incontinence, reducing the risk of acquiring urinary incontinence or at least one of the clinical symptoms of urinary incontinence, inhibiting the progress of urinary incontinence or at least one of the clinical symptoms of urinary incontinence, or reducing the risk of developing urinary incontinence or at least one of the clinical symptoms of urinary incontinence. "Treating" or "treatment" also refers to inhibiting urinary incontinence, either physically (e.g., stabilization of a discernible symptom), physiologically (e.g., stabilization of a physical parameter), or both, and to inhibiting at least one physical parameter that may or may not be discernible to the patient. In certain embodiments, "treating" or "treatment" refers to delaying the onset of urinary incontinence or at least one or more symptoms thereof in a patient who may be exposed to, or predisposed to, urinary incontinence even though that patient does not yet experience or display symptoms of urinary incontinence.

"Therapeutically effective amount" refers to the amount of (3R)-4-{[(1S)-2-methyl-1-(2-methylpropanoyloxy)propoxy]carbonylamino}-3-(4-chlorophenyl)butanoic acid that, when administered to a subject for treating urinary incontinence, or at least one of the clinical symptoms of urinary incontinence, is sufficient to affect such treatment of urinary incontinence or symptom thereof. The "therapeutically effective amount" may vary depending, for example, the type of urinary incontinence and/or symptoms of the urinary incontinence, severity of the urinary incontinence and/or symptoms of the urinary incontinence, the age, weight, and/or health of the patient to be treated, and the judgment of the prescribing physician. A therapeutically effective amount in any given instance may be ascertained by those skilled in the art and/or is capable of determination by routine experimentation.

Reference is now made in detail to certain embodiments of compounds, compositions, and methods. The disclosed embodiments are not intended to be limiting of the claims. To the contrary, the claims are intended to cover all alternatives, modifications, and equivalents.

Urinary Incontinence

Urinary incontinence is any involuntary leakage of urine and can be categorized into the following five types based on the pattern of symptoms: urge incontinence, stress incontinence, overflow incontinence, functional incontinence, and mixed incontinence. Abrams et al., *Neurology and Urodynamics* (2002), 21, 167-178.

Urge incontinence is an abrupt and intense urge to urinate that cannot be suppressed, followed by an uncontrollable loss of urine. Urge incontinence can be caused by a combination of overactivity of the muscles in the bladder along with poor squeezing ability of the bladder muscles in part due to changes in the part of the brain in the frontal lobe that inhibits urination. Involuntary actions of bladder muscles can occur because of damage to the nerves of the bladder, to the nervous system including the spinal cord and brain, or to the muscles themselves. Damage to the muscles and nerves may occur as the result of stroke, surgery, or brain disorders such as multiple sclerosis, Parkinson's disease, Alzheimer's disease.

Stress incontinence is the uncontrollable loss of small amounts of urine when coughing, straining, sneezing, lifting heavy objects, or performing any maneuver that suddenly increases pressure within the abdomen and is generally caused by insufficient strength of the pelvic floor muscles. Incontinence following prostate surgery is the most common form of stress incontinence in men. In women, stress incontinence can result from physical changes associated with pregnancy, childbirth, menopause, or pelvic surgery.

Overflow incontinence is the uncontrollable leakage of small amounts of urine, usually caused by some type of blockage or by weak contractions of the bladder muscles. Overflow incontinence can be caused by prostate surgery, enlarged prostate, constipation, nerve damage, drugs that affect the brain or spinal cord that interfere with nerve messages, diabetes, multiple sclerosis, tumors, spinal cord injuries, nervous system disorders, and diseases such as multiple sclerosis that can decrease neural signals from the bladder or the expulsion of urine by the detrusor muscle.

Functional incontinence refers to urine loss resulting from the physical inability or unwillingness to get to the toilet due to limited mobility. Causes of functional incontinence include confusion, dementia, poor eyesight, poor mobility, poor dexterity, unwillingness to toilet due to depression, anxiety, anger, drunkenness, or physical impossibility such as a person in a wheelchair. Conditions causing immobility include stroke, severe arthritis, and contentions that interfere with mental function such as dementia due to Alzheimer's disease and severe depression.

Mixed urinary incontinence involves more than one type of incontinence.

Urinary incontinence also includes bedwetting, also known as enuresis.

Urinary incontinence also includes overactive bladder. Overactive bladder is characterized by urgency, with or without urge incontinence, usually with frequency incontinence and nocturia. Abrams, *Urology* (2003), 62 (Supp. 5B) 28-37: Ouslander *N Engl J Med* (2004), 350, 786-99: Wein and Rovner *Urology* (2002) (Supp. 5A), 7-12. With respect to overactive bladder, urgency can be defined as the complaint by a patient of a sudden compelling desire to void; frequency can be defined as the complaint by a patient who considers that he/she voids too often by day; and nocturia can be defined as the complaint by a patient that he/she has to wake more than about one time during the night to void. Patients with overactive bladder thus typically present with symptoms of a sudden and compelling need to urinate which is difficult to defer (urgency), involuntary leakage of urine with feelings of urgency (urge urinary incontinence), frequency ($\geq 8$ micturitions in 24 hours) and nocturia ($\geq$ one awakening per night to void). The symptoms of overactive bladder are due to involuntary contractions of the detrusor muscle during the filling phase of the micturition cycle that may be spontaneous or provoked. These involuntary contractions are termed detrusor overactivity and are mediated by acetylcholine-induced stimulation of bladder muscarinic receptors. Andersson, *Urology* (1997), 50 (Supp. 6A), 74-84. Detrusor overactivity can be characterized as either idiopathic detrusor overactivity, where there is no defined underlying cause, and detrusor overactivity, where there is a relevant neurologic condition.

Interstitial cystitis, also termed painful bladder syndrome, is a disorder related to urinary incontinence. Interstitial cystitis is a chronic inflammatory condition of the bladder believed to be caused by many factors including autoimmune, allergic, and infectious etiologies. Symptoms of interstitial cystitis include excessive urgency to urinate even after the patient has voided, urinary frequency averaging 16 times per day or greater, nighttime urination, suprapubic (bladder/pelvic/perineal) pain, and dyspareunia.

Therapeutic Uses; Synthesis (3R)-4-{[(1S)-2-Methyl-1-(2-methylpropanoyloxy)propoxy]carbonylamino}-3-(4-chlorophenyl)butanoic acid may be used to treat urinary incontinence. In certain embodiments, (3R)-4-{[(1S)-2-methyl-1-(2-methylpropanoyloxy)propoxy]carbonylamino}-3-(4-chlorophenyl)butanoic acid and pharmaceutical compositions provided by the present disclosure may be used to treat interstitial cystitis. In certain embodiments, the (3R)-4-{[(1S)-2-Methyl-1-(2-methylpropanoyloxy)propoxy]carbonylamino}-3-(4-chlorophenyl)butanoic acid is crystalline. In certain embodiments, (3R)-4-{[(1S)-2-methyl-1-(2-methylpropanoyloxy)propoxy]carbonylamino}-3-(4-chlorophenyl)butanoic acid may be used to treat urinary incontinence, and in certain embodiments, crystalline (3R)-4-{[(1S)-2-methyl-1-(2-methylpropanoyloxy)propoxy]carbonylamino}-3-(4-chlorophenyl)butanoic acid may be used to treat urinary incontinence.

Methods of treating urinary incontinence in a patient provided by the present disclosure comprise administering to a patient in need of such treatment a therapeutically effective amount of (3R)-4-{[(1S)-2-methyl-1-(2-methylpropanoyloxy)propoxy]carbonylamino}-3-(4-chlorophenyl)butanoic acid or pharmaceutically acceptable salt thereof, or a pharmaceutical composition comprising any of the foregoing. (3R)-4-{[(1S)-2-Methyl-1-(2-methylpropanoyloxy)propoxy]carbonylamino}-3-(4-chlorophenyl)butanoic acid or pharmaceutical compositions thereof may provide therapeutic or prophylactic plasma and/or blood concentrations of (R)-baclofen following administration to a patient.

Methods of using (3R)-4-{[(1S)-2-methyl-1-(2-methylpropanoyloxy)propoxy]carbonylamino}-3-(4-chlorophenyl)butanoic acid to treat diseases such as spasticity, gastroesophageal reflux disease, neuropathic pain, and musculoskeletal pain are disclosed in U.S. Pat. Nos. 7,109,239; 7,300,956; 7,572,830: US 2009/0234138: US 2009/0041806: and US 2009/0118365.

Methods of synthesizing (3R)-4-{[(1S)-2-methyl-1-(2-methylpropanoyloxy)propoxy]carbonylamino}-3-(4-chlorophenyl)butanoic acid are disclosed in U.S. Pat. Nos. 7,109, 239; 7,227,028: US 2009/0192325: US 2010/0087667: and US 2010/0081830.

Pharmaceutical Compositions

Pharmaceutical compositions provided by the present disclosure may comprise a therapeutically effective amount of (3R)-4-{[(1S)-2-methyl-1-(2-methylpropanoyloxy)propoxy]carbonylamino}-3-(4-chlorophenyl)butanoic acid together with a suitable amount of one or more pharmaceutically acceptable vehicles so as to provide a composition for proper administration to a patient. Suitable pharmaceutical vehicles include, for example, excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

(3R)-4-{[(1S)-2-Methyl-1-(2-methylpropanoyloxy)propoxy]carbonylamino}-3-(4-chlorophenyl)butanoic acid may be incorporated into pharmaceutical compositions to be administered by any appropriate route of administration including intradermal, intramuscular, intraperitoneal, intravenous, subcutaneous, intranasal, epidural, oral, sublingual, intracerebral, intravaginal, transdermal, rectal, inhalation, or topical.

In certain embodiments, (3R)-4-{[(1S)-2-methyl-1-(2-methylpropanoyloxy)propoxy]carbonylamino}-3-(4-chlorophenyl)butanoic acid may be incorporated into pharmaceutical compositions to be administered orally. Oral administration of such pharmaceutical compositions may result in uptake of (3R)-4-{[(1S)-2-methyl-1-(2-methylpropanoyloxy)propoxy]carbonylamino}-3-(4-chlorophenyl)butanoic acid throughout the intestine and entry into the systemic circulation. Such oral compositions may be prepared by means of conventional mixing, dissolving, granulating, dragee making, levigating, emulsifying, encapsulating, entrapping or lyophilizing processes. Pharmaceutical compositions may be formulated in a conventional manner using one or more physiologically acceptable carriers, diluents, excipients or auxiliaries, which facilitate the processing of (3R)-4-{[(1S)-2-methyl-1-(2-methylpropanoyloxy)propoxy]carbonylamino}-3-(4-chlorophenyl)butanoic acid into preparations which can be used pharmaceutically. Proper formulation is dependent upon the route of administration chosen.

The present pharmaceutical compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). In some embodiments, compositions are formulated for oral delivery, for example for oral sustained release administration.

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. which, in certain embodiments, are of pharmaceutical grade. Oral pharmaceutical compositions may include a therapeutically effective amount of (3R)-4-{[(1S)-2-methyl-1-(2-methylpropanoyloxy)propoxy]carbonylamino}-3-(4-chlorophenyl)butanoic acid and a suitable amount of a pharmaceutically acceptable vehicle.

In certain embodiments, pharmaceutical compositions comprising (3R)-4-{[(1S)-2-methyl-1-(2-methylpropanoyloxy)propoxy]carbonylamino}-3-(4-chlorophenyl)butanoic acid may be formulated for immediate release.

Dosage Forms; Dosing

Pharmaceutical compositions provided by the present disclosure may be formulated in a unit dosage form. A unit dosage form refers to a physically discrete unit suitable as a unitary dose for patients undergoing treatment, with each unit containing a predetermined quantity of (3R)-4-{[(1S)-2-methyl-1-(2-methylpropanoyloxy)propoxy]carbonylamino}-3-(4-chlorophenyl)butanoic acid calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug at a particular rate. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of (3R)-4-{[(1S)-2-methyl-1-(2-methylpropanoyloxy)propoxy]carbonylamino}-3-(4-chlorophenyl)butanoic acid, the stability of (3R)-4-{[(1S)-2-methyl-1-(2-methylpropanoyloxy)propoxy]carbonylamino}-3-(4-chlorophenyl)butanoic acid in the gastrointestinal tract, the pharmacokinetics of (3R)-4-{[(1S)-2-methyl-1-(2-methylpropanoyloxy)propoxy]carbonylamino}-3-(4-chlorophenyl)butanoic acid, and/or the intended therapeutic profile. Based on the foregoing considerations, an appropriate controlled release oral dosage form may be selected. For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be formulated in dosage forms adapted to provide sustained release of (3R)-4-{[(1S)-2-methyl-1-(2-methylpropanoyloxy)propoxy]carbonylamino}-3-(4-chlorophenyl)butanoic acid upon oral administration. Sustained release oral dosage forms may be used to release drugs over a prolonged time period such as at least 6 hours, at least 8 hours, at least 10 hours, or at least 12 hours, and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Sustained release oral dosage forms comprising (3R)-4-{[(1S)-2-methyl-1-(2-methylpropanoyloxy)propoxy]carbonylamino}-3-(4-chlorophenyl)butanoic acid are disclosed in US 2008/0206332, US 2009/0197958, and US 2010/0255093.

In certain embodiments, dosage forms provided by the present disclosure may be administered once per day, twice per day, and in certain embodiments at intervals of more than once per day.

A dose of (3R)-4-{[(1S)-2-methyl-1-(2-methylpropanoyloxy)propoxy]carbonylamino}-3-(4-chlorophenyl)butanoic acid can be adjusted to provide an equivalent molar quantity or mass equivalent dose of (R)-baclofen. A dose can comprise multiple dosage forms provided by the present disclosure. In certain embodiments, therapeutically effective doses of (R)-baclofen are generally from about 0.03 mg to about 1 mg per kilogram body weight per day. In certain embodiments, a daily dose can comprise a mass equivalent of (R)-baclofen ranging from about 1 mg to about 100 mg; in certain embodiments from about 5 mg to about 80 mg; in certain embodiments from about 5 mg to about 60 mg; and in certain embodiments from about 10 mg to about 40 mg. In certain embodiments, a dose of (3R)-4-{[(1S)-2-methyl-1-(2-methylpropanoyloxy)propoxy]carbonylamino}-3-(4-chlorophenyl)butanoic acid is less than a dose that causes moderate sedation and impairment of motor activity in a patient. The dose of (3R)-4-{[(1S)-2-methyl-1-(2-methylpropanoyloxy)propoxy]carbonylamino}-3-(4-chlorophenyl)butanoic acid and appropriate dosing intervals can be selected to maintain a sustained therapeutically effective concentration of (R)-baclofen in the blood of a patient, and in certain embodiments, without exceeding a minimum adverse concentration.

Dosing may be provided alone or in combination with other drugs and may continue as long as required for effective treatment of the disease. Dosing includes administering a dosage form to a mammal, such as a human, in a fed or fasted state.

A dose may be administered in a single dosage form or in multiple dosage forms. When multiple dosage forms are used the amount of (3R)-4-{[(1S)-2-methyl-1-(2-methylpropanoyloxy)propoxy]carbonylamino}-3-(4-chlorophenyl)butanoic acid within each of the multiple dosage forms may be the same or different.

In certain embodiments, a therapeutically effective dose of (3R)-4-{[(1S)-2-methyl-1-(2-methylpropanoyloxy)propoxy]carbonylamino}-3-(4-chlorophenyl)butanoic acid may provide therapeutic benefit without causing substantial toxicity including adverse side effects. Toxicity of (3R)-4-{[(1S)-2-methyl-1-(2-methylpropanoyloxy)propoxy]carbonylamino}-3-(4-chlorophenyl)butanoic acid, and/or metabolites thereof may be determined using standard pharmaceutical procedures and may be ascertained by one skilled in the art. The dose ratio between toxic and therapeutic effect is the therapeutic index. A dose of (3R)-4-{[(1S)-2-methyl-1-(2-methylpropanoyloxy)propoxy]carbonylamino}-3-(4-chlorophenyl)butanoic acid may be within a range capable of establishing and maintaining a therapeutically effective circulating plasma and/or blood concentration of (3R)-4-{[(1S)-2-methyl-1-(2-methylpropanoyloxy)propoxy]carbonylamino}-3-(4-chlorophenyl)butanoic acid that exhibits little or no toxicity or adverse effects.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One skilled in the art may optimize administration to humans based on animal data.

Additionally, an appropriate dose of (3R)-4-{[(1S)-2-methyl-1-(2-methylpropanoyloxy)propoxy]carbonylamino}-3-(4-chlorophenyl)butanoic acid, or of a pharmaceutical composition comprising (3R)-4-{[(1S)-2-methyl-1-(2-methylpropanoyloxy)propoxy]carbonylamino}-3-(4-chlorophenyl)butanoic acid, may be determined according to any one of several well-established protocols. For example, animal studies such as studies using mice, rats, dogs, and/or monkeys may be performed to determine an appropriate dose of a pharmaceutical compound. Results from animal studies may be extrapolated to determine doses for use in other species, such as for example, humans.

For example, (3R)-4-{[(1S)-2-Methyl-1-(2-methylpropanoyloxy)propoxy]carbonylamino}-3-(4-chlorophenyl)butanoic acid may be assayed in vitro and in vivo for the desired therapeutic or prophylactic activity prior to use in humans. In vivo assays, for example using appropriate animal models, may also be used to determine whether administration of (3R)-4-{[(1S)-2-methyl-1-(2-methylpropanoyloxy)propoxy]carbonylamino}-3-(4-chlorophenyl)butanoic acid is therapeutically effective. The efficacy of (3R)-4-{[(1S)-2-methyl-1-(2-methylpropanoyloxy)propoxy]carbonylamino}-3-(4-chlorophenyl)butanoic acid for treating urinary incontinence may be determined using animal models (Pehrson et al., *J Urology* 2002, 168, 2700-2705: Igawa et al., *J Urology* 1993, 150, 537-542: Santicioli et al., *J Pharm Pharmacol* 1984, 36, 378-381: and Hijaz et al., *J Urology* 2008, 179(6), 2103-2110) or in clinical trials.

Modes of Administration (3R)-4-{[(1S)-2-Methyl-1-(2-methylpropanoyloxy)propoxy]carbonylamino}-3-(4-chlorophenyl)butanoic acid and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known, e.g., encapsulation in liposomes, microparticles, microcapsules, capsules, etc., that may be used to administer a compound and/or pharmaceutical composition.

The amount of (3R)-4-{[(1S)-2-methyl-1-(2-methylpropanoyloxy)propoxy]carbonylamino}-3-(4-chlorophenyl)butanoic acid that will be effective in the treatment of urinary incontinence in a patient will depend, in part, on the type of urinary incontinence and can be determined by standard clinical techniques known in the art. A therapeutically effective amount of (3R)-4-{[(1S)-2-methyl-1-(2-methylpropanoyloxy)propoxy]carbonylamino}-3-(4-chlorophenyl)butanoic acid to be administered may also depend on, among other factors, the subject being treated, the weight of the subject, the severity of the disease, the manner of administration, and the judgment of the prescribing physician.

Combination Therapy

Methods provided by the present disclosure may further comprise administering one or more pharmaceutically active compounds in addition to (3R)-4-{[(1S)-2-methyl-1-(2-methylpropanoyloxy)propoxy]carbonylamino}-3-(4-chlorophenyl)butanoic acid. Such additional pharmaceutically active compounds may be provided to treat urinary incontinence, a different disease or both.

Accordingly, in certain embodiments, (3R)-4-{[(1S)-2-methyl-1-(2-methylpropanoyloxy)propoxy]carbonylamino}-3-(4-chlorophenyl)butanoic acid may be used in combination with at least one other therapeutic agent. (3R)-4-{[(1S)-2-Methyl-1-(2-methylpropanoyloxy)propoxy]carbonylamino}-3-(4-chlorophenyl)butanoic acid and the at least one other therapeutic agent may act additively or, in certain embodiments, synergistically. The at least one additional therapeutic agent may be included in the same dosage form as (3R)-4-{[(1S)-2-methyl-1-(2-methylpropanoyloxy)propoxy]carbonylamino}-3-(4-chlorophenyl)butanoic acid or may be in a separate dosage form. Methods provided by the present disclosure include administration of (3R)-4-{[(1S)-2-methyl-1-(2-methylpropanoyloxy)propoxy]carbonylamino}-3-(4-chlorophenyl)butanoic acid and one or more other therapeutic agents provided that the combined administration does not inhibit the therapeutic efficacy of (3R)-4-{[(1S)-2-methyl-1-(2-methylpropanoyloxy)propoxy]carbonylamino}-3-(4-chlorophenyl)butanoic acid and/or does not produce adverse combination effects.

In certain embodiments, dosage forms comprising (3R)-4-{[1S)-2-methyl-1-(2-methylpropanoyloxy)propoxy]carbonylamino}-3-(4-chlorophenyl)butanoic acid may be administered concurrently with the administration of another therapeutic agent, which may be part of the same dosage form as, or in a different dosage form than that comprising (3R)-4-{[(1S)-2-methyl-1-(2-methylpropanoyloxy)propoxy]carbonylamino}-3-(4-chlorophenyl) butanoic acid. (3R)-4-{[(1S)-2-Methyl-1-(2-methylpropanoyloxy)propoxy]carbonylamino}-3-(4-chlorophenyl)butanoic acid may be administered prior or subsequent to administration of another therapeutic agent. In certain embodiments of combination therapy, the combination therapy may comprise alternating between administering (3R)-4-{[(1S)-2-methyl-1-(2-methylpropanoyloxy)propoxy]carbonylamino}-3-(4-chlorophenyl)butanoic acid and a composition comprising another therapeutic agent, e.g., to minimize adverse drug effects associated with a particular drug. When (3R)-4-{[(1S)-2-methyl-1-(2-methylpropanoyloxy)propoxy]carbonylamino}-3-(4-chlorophenyl)butanoic acid is administered concurrently with another therapeutic agent that potentially may produce an adverse drug effect including, but not limited to, toxicity, the other therapeutic agent may be administered at a dose that falls below the threshold at which the adverse drug reaction is elicited.

In certain embodiments, dosage forms comprising (3R)-4-{[1S)-2-methyl-1-(2-methylpropanoyloxy)propoxy]carbonylamino}-3-(4-chlorophenyl)butanoic acid may be administered with one or more substances to enhance, modulate and/or control release, bioavailability, therapeutic efficacy, therapeutic potency, stability, and the like of (3R)-4-{[(1S)-2-methyl-1-(2-methylpropanoyloxy)propoxy]carbonylamino}-3-(4-chlorophenyl) butanoic acid. For example, to enhance the therapeutic efficacy of (3R)-4-{[(1S)-2-methyl-1-(2-methylpropanoyloxy)propoxy]carbonylamino}-3-(4-chlorophenyl)butanoic acid, (3R)-4-{[(1S)-2-methyl-1-(2-methylpropanoyloxy)propoxy]carbonylamino}-3-(4-chlorophenyl) butanoic acid may be co-administered with, or a dosage form comprising (3R)-4-{[(1S)-2-methyl-1-(2-methylpropanoyloxy)propoxy]carbonylamino}-3-(4-chlorophenyl)butanoic acid may comprise, one or more active agents that serve to increase the absorption or diffusion of (3R)-4-{[(1S)-2-methyl-1-(2-methylpropanoyloxy)propoxy]carbonylamino}-3-(4-chlorophenyl) butanoic acid from the gastrointestinal tract to the systemic circulation, or to inhibit degradation of (3R)-4-{[(1S)-2-methyl-1-(2-methylpropanoyloxy)propoxy]carbonylamino}-3-(4-chlorophenyl)butanoic acid in the blood of a patient. In certain embodiments, (3R)-4-{[(1S)-2-methyl-1-(2-methylpropanoyloxy)propoxy]carbonylamino}-3-(4-chlorophenyl)butanoic acid may be co-administered with an active agent having pharmacological effects that enhance the therapeutic efficacy of (3R)-4-{[(1S)-2-methyl-1-(2-methylpropanoyloxy)propoxy]carbonylamino}-3-(4-chlorophenyl)butanoic acid.

Additionally, dosage forms provided by the present disclosure may be used in combination with other drugs that are themselves known to cause urinary incontinence, either directly or as a side effect, thereby preventing or reducing the occurrence of such adverse effects.

In certain embodiments, (3R)-4-{[(1S)-2-methyl-1-(2-methylpropanoyloxy)propoxy]carbonylamino}-3-(4-chlorophenyl)butanoic acid or a pharmaceutical composition thereof may be administered to a patient for treating urinary incontinence in combination with a therapy or another therapeutic agent known or believed to be effective in treating urinary incontinence. Examples of drugs useful for treating urinary incontinence, and which may be administered in conjunction with (3R)-4-{[(1S)-2-methyl-1-(2-methylpropanoyloxy)propoxy]carbonylamino}-3-(4-chlorophenyl)butanoic acid, include amitriptyline, belladonna, darifenacin, desmopressin, duloxetine, estrogen, fesoterodine, flavoxate, hyoscyamine, imidafenacin, imipramine, nitrofurantoin, oxybutynin, propiverine, solaberon, solifenacin, tamsulosin hydrochloride, tamsulosin, tolterodine, trospium, type A botulinum toxin, and vardenafil hydrochloride. Other drugs that show potential for treating urinary incontinence, and in particular overactive bladder, include drugs acting on $K^+$ channels such as NS-8, KW-7158, ZD-0947; $5-HT_3$ antagonists; $5-HT_{1a}$ antagonists such as REC-0545: P2X antagonists; NK1 receptor antagonists such as SSR-240600, TA-5538, and aprepitant; β3-agonists such as GW-427353 and KUC-7483, YM-178: and others such as DDP-200 (oxybutynin and gabapentin), nitroflurbiprofen, elocalcitol, NCX-2111, and besipirdine. Colli et al., *Expert Opin Investig Drugs* (2007), 16(7), 999-1007. β$_3$-Adrenoceptor agonists have also recently been proposed for the treatment of overactive bladder. Tyagi et al., *Drugs of the Future* (2009), 34(8), 635-640. Other drugs useful for treating urinary incontinence are disclosed in Robinson and Cardozo, *Maturitas* (2010) doi: 10.1016/j.maturitas.2009.12.022.

EXAMPLES

The following examples describe in detail the synthesis of (3R)-4-{[(1S)-2-methyl-1-(2-methylpropanoyloxy)propoxy]carbonylamino}-3-(4-chlorophenyl)butanoic acid. It will be apparent to those skilled in the art that modifications, both to materials and methods, may be practiced without departing from the scope of the disclosure.

General Synthetic Protocols

All reagents and solvents were purchased from commercial suppliers and used without further purification or manipulation prior to use.

Proton NMR spectra (400 MHz) were recorded on a Varian AS 400 NMR spectrometer equipped with an autosampler and data processing computation. DMSO-$d^6$ (99.9% D) or CDCl$_3$ (99.8% D) were used as solvents unless otherwise noted. The DMSO-$d^5$ or CHCl$_3$ solvent signal was used for calibration of the individual spectra. Analytical LC/MS was performed on a Waters 2790 separation module equipped with a Waters Micromass QZ mass spectrometer, a Waters 996 photodiode detector, and a Merck Chromolith UM2072-027 or Phenomenex Luna C-18 analytical column. Analytical thin layer chromatography (TLC) was performed using Whatman, Schleicher & Schuell TLC MK6F silica gel plates (2.5×7.5 cm, 250 μm layer thickness). Mass-guided preparative HPLC purification of titled compounds was performed on an instrument equipped with a Waters 600 controller, ZMD Micromass spectrometer, a Waters 2996 photodiode array detector, and a Waters 2700 Sample Manager. Acetonitrile/water gradients containing 0.05% formic acid were used as eluants in both analytical and preparative HPLC experiments unless noted otherwise.

Example 1

Synthesis of O-(1-Isobutanoyloxyisobutoxy)S-Methyl Thiocarbonate (1)

Step A: O-(1-Chloroisobutoxy)S-methyl thiocarbonate (1a)

A solution of 1-chloro-2-methylpropyl chloroformate (1026 g, 6.0 mol) and tetrabutylammonium hydrogensulfate (20 g, 60 mmol) in dichloromethane (1500 mL) in a jacketed 10 L reactor equipped with a mechanical stirrer, temperature probe, and addition funnel was cooled to 10° C. To the reaction mixture was gradually added a 15% aqueous solution of sodium methylthiolate (3 L, 6.4 mol) over 4 h. The reaction was moderately exothermic and the internal temperature was maintained between 10° C. and 20° C. during the addition. The aqueous phase was separated and the organic phase was washed with brine (2×2 L) and water (2 L). The organic layer was dried over anhydrous $Na_2SO_4$, filtered, and concentrated under reduced pressure to afford the title compound (1a) (1050 g, 5.76 mol, 96%) as a colorless liquid. $^1$H NMR ($CDCl_3$, 400 MHz): δ 1.1 (dd, 6H), 2.2 (m, 1H), 2.4 (s, 3H), 6.35 (d, 1H).

Step B: Tetramethylammonium isobutyrate (1b)

To a 20 L, round bottom flask was added isobutyric acid (1300 mL, 14 mol), and an aqueous solution of 25% tetramethylammonium hydroxide (5 L, 14 mol). The water was removed under reduced pressure, and azeotroped with toluene (2×2 L) to leave the product (1b) as an amber liquid, which was used without further purification.

Step C: O-(1-Isobutanoyloxyisobutoxy)S-Methyl Thiocarbonate (1)

To a 3 L, three neck, round bottom flask equipped with a mechanical stirrer and Teflon-coated thermocouple was added (1b) (1672 g, 9 mol), isobutyric acid (264 g, 1.5 mol), and (1a) (1050 g, 5.76 mol). The reaction mixture was heated to 80° C. for 12 h, monitoring the reaction progress by $^1$H NMR. The reaction mixture was cooled to 20° C., diluted with EtOAc (1 L) and washed with water (2×1 L), saturated $NaHCO_3$ (1×2 L) and water (1 L). The organic phase was separated and concentrated under reduced pressure to afford the product (1) (905 g, 3.9 mol, 65%) as a colorless liquid. $^1$H NMR ($CDCl_3$, 400 MHz): δ 1.0 (d, 6H), 1.2 (dd, 6H), 2.05 (m, 1H), 2.35 (s, 3H), 2.6 (m, 1H), 6.7 (d, 1H).

Example 2

Synthesis of (1S)-[((3S,4S)-2,5-Dioxo-3,4-diisobutyroyloxypyrrolidinyl)-oxycarbonyloxy]-2-methyl propyl 2-methylpropanoate (2)

Step A: (3S,4S)-2,5-Dioxo-3,4-diisobutyroyloxy-3,4-dihydrofuran (2a)

To a suspension of D-tartaric acid (5.0 g, 33.3 mmol) in toluene (60 mL) was added isobutyryl chloride (11.3 mL, 107 mmol). The resulting suspension was heated to reflux and stirred for 22 h at reflux temperature. The reaction mixture was then concentrated in vacuo to afford a crystalline solid, which was suspended in a mixture of ether and hexane (1:3), filtered, washed with hexane and dried to afford the desired compound (2a) as a white crystalline solid (6.4 g, 71%). $^1$H-NMR (400 MHz, $CDCl_3$): δ 1.25 (d, J=6.8 Hz, 12H), 2.72 (hept, J=6.8 Hz, 2H), 5.63 (s, 2H).

Step B: 1-Hydroxy-(3S,4S)-2,5-dioxo-3,4-diisobutyroyloxypyrrolidine (2b)

To a stirred solution of compound (2a) (5.98 g, 22 mmol) in ethyl acetate (50 mL) at 0° C. was added a 50% aqueous solution of hydroxylamine (1.75 g, 26.4 mmol). The resulting mixture was stirred at room temperature for 3 h and washed successively with aqueous citric acid solution and brine, then dried over anhydrous sodium sulfate. After filtration and concentration in vacuo, the residue was suspended in toluene and the reaction mixture heated under reflux for 5 h, with the azeotropically liberated water being collected in a Dean-Stark apparatus. Toluene was removed in vacuo to afford the title compound (2b) (6.3 g, quantitative yield). $^1$H-NMR (400 MHz, $CDCl_3$): δ 1.22 (d, J=6.8 Hz, 12H), 2.69 (hept, J=6.8 Hz, 2H), 5.48 (s, 2H).

Step C: (1S)-1-[((3S,4S)-2,5-Dioxo-3,4-diisobutryoyloxypyrrolidinyl)-oxycarbonyloxy]-2-methyl propyl 2-methylpropanoate (2)

To a stirred solution of compound (2b) (4.89 g, 17.0 mmol) and thiocarbonate (1) (4.39 g, 18 7 mmol) in $CH_2Cl_2$ at 0° C. was added dropwise a 32% solution of peracetic acid in acetic acid (10.74 mL, 51.06 mmol). The resulting reaction mixture was stirred at 0° C. to room temperature for 21 h, monitoring the reaction progress by NMR. The reaction mixture was washed with water and brine, then dried over anhydrous sodium sulfate. After removal of the solvent in vacuo, the crude product was filtered through a short silica gel column, eluting with 20% ethyl acetate in hexane to afford the desired compound as a mixture of diastereomers. The mixture was carefully crystallized from 5% ether in hexane to afford the title compound (2). The diastereomeric purity of the product was determined to be ca. 84% d.e. by HPLC using a chiral column. An additional recrystallization affords a product having greater diastereomeric purity. $^1$H-NMR (400 MHz, $CDCl_3$): δ 1.04 (d, J=6.8 Hz, 6H), 1.20 (d, J=6.8 Hz, 6H), 1.24 (d, J=6.8 Hz, 6H), 1.26 (d, J=6.8 Hz, 6H), 2.17 (m, 1H), 2.62 (hept, J=6.8 Hz, 1H), 2.70 (hept, J=6.8 Hz, 2H), 5.63 (br.s, 2H), 6.60 (d, J=5.2 Hz, 1H).

Example 3

Synthesis of 4-{[(1S)-Isobutanoyloxyisobutoxy]carbonylamino}-(3R)-(4-chlorophenyl)-butanoic Acid (3)

A suspension of (1S)-1-[((3S,4S)-2,5-dioxo-3,4-diisobutryoyloxypyrrolidinyl)-oxycarbonyloxy]-2-methylpropyl 2-methylpropanoate, (2) and (R)-baclofen in 10% v/v water-acetonitrile was stirred at room temperature for 4 h. Acetonitrile was removed in vacuo to afford the crude product, which was partitioned between water and ethyl acetate. The organic layer was washed with water (3×) and brine then dried over anhydrous sodium sulfate. After removal of the solvent in vacuo, the product was crystallized from 20% ethyl acetate-hexane to afford the title compound (3). The diastereomeric purity of the product was determined to be ~92% d.e. by HPLC using a chiral column.

Example 4

Synthesis of O-(1-Isobutanoyloxyisobutoxy)S-methyl thiocarbonate (4)

Step A: O-(1-Chloroisobutoxy)S-methyl thiocarbonate (4a)

A solution of 1-chloro-2-methylpropyl chloroformate (1026 g, 6.0 mol) and tetrabutylammonium hydrogensulfate (20 g, 60 mmol) in dichloromethane (1500 mL) in a jacketed 10 L reactor equipped with a mechanical stirrer, temperature probe, and addition funnel was cooled to 10° C. To the reaction mixture was gradually added a 15% aqueous solution of sodium methylthiolate (3 L, 6.4 mol) over 4 h. The reaction was moderately exothermic and the internal temperature was maintained between 10° C. and 20° C. during the addition. The aqueous phase was separated and the organic phase was washed with brine (2×2 L) and water (2 L). The organic layer was dried over anhydrous $Na_2SO_4$, filtered, and concentrated under reduced pressure to afford the title compound (4a) (1050 g, 5.76 mol, 96%) as a colorless liquid. $^1$H NMR ($CDCl_3$, 400 MHz): δ 1.1 (dd, 6H), 2.2 (m, 1H), 2.4 (s, 3H), 6.35 (d, 1H).

Step B: Tetramethylammonium isobutyrate (4b)

To a 20 L, round bottom flask was added isobutyric acid (1300 mL, 14 mol), and an aqueous solution of 25% tetramethylammonium hydroxide (5 L, 14 mol). The water was removed under reduced pressure, and azeotroped with toluene (2×2 L) to leave the product (4b) as an amber liquid, which was used without further purification.

Step C: O-(1-Isobutanoyloxyisobutoxy)S-methyl thiocarbonate (4)

To a 3 L, three neck, round bottom flask equipped with a mechanical stirrer and Teflon-coated thermocouple was added (4b) (1672 g, 9 mol), isobutyric acid (264 g, 1.5 mol), and (4a) (1050 g, 5.76 mol). The reaction mixture was heated to 80° C. for 12 h, monitoring the reaction progress by $^1$H NMR. The reaction mixture was cooled to 20° C., diluted with EtOAc (1 L) and washed with water (2×1 L), saturated $NaHCO_3$ (1×2 L) and water (1 L). The organic phase was separated and concentrated under reduced pressure to afford the product (4) (905 g, 3.9 mol, 65%) as a colorless liquid. $^1$H NMR ($CDCl_3$, 400 MHz): δ 1.0 (d, 6H), 1.2 (dd, 6H), 2.05 (m, 1H), 2.35 (s, 3H), 2.6 (m, 1H), 6.7 (d, 1H).

Example 5

Synthesis of (1S)-1-1[((3R,4R)-2,5-Dioxo-3,4-dibenzoyloxypyrrolidinyl)-oxycarbonyloxy]-2-methylpropyl 2-methylpropanoate (5)

Step A: (3R,4R)-2,5-Dioxo-3,4-dibenzoyloxy-3,4-dihydrofuran (5a)

To a 3-necked, 5 L, round bottom flask fitted with a mechanical stirrer and a Teflon-coated thermocouple was added (−)-2,3-dibenzoyl-L-tartaric acid (1000 g, 2.79 mol) followed by acetic anhydride (2 L). The suspension was stirred and heated to 85° C. for 2 h during which time the starting material gradually dissolved. A short time thereafter, the product began to crystallize in the reaction mixture and the suspension was then cooled to 25° C. The product was collected by filtration, washed with 10% acetone in hexane (2×1 L), and dried in a vacuum oven at 50° C. overnight to afford the title compound (5a) as a white solid. $^1$H NMR ($CDCl_3$, 400 MHz): δ 6.0 (s, 2H), 7.45 (app. t, 4H), 7.65 (app. t, 2H), 8.05 (d, 4H).

Step B: 1-Hydroxy-(3R,4R)-2,5-dioxo-3,4-dibenzoyloxypyrrolidine (5b)

To a 3-neck, 5 L, round bottom flask fitted with a mechanical stirrer and a Teflon-coated temperature probe was added (5a) (2.79 mol) followed by acetonitrile (2 L). The suspension was cooled in an ice bath to 4° C., followed by the addition of 50% aqueous hydroxylamine (180 mL, 2.93 mol) over 1 h. The starting material gradually dissolved during the addition and the reaction mixture was warmed to 20° C. and stirred for 1 h. The reaction mixture was concentrated in vacuo, diluted with EtOAc (1 L) and washed with 1 N HCl (2×1 L). The organic phase was separated and concentrated in vacuo to afford a viscous red syrup. The syrup was then heated for two hours in toluene (2.5 L) at 100° C. with azeotropic removal of water. The syrup gradually dissolved and then the product crystallized. After cooling to room temperature the solid was collected by filtration, washed with 10% acetone in hexane (2×1 L) and dried in a vacuum oven to afford the title compound (5b) (862 g, 2.43 mol, 87%) as a white solid. $^1$H NMR ($CDCl_3$, 400 MHz): δ 5.85 (s, 2H), 7.45 (app. t, 4H), 7.65 (app t, 2H), 8.05 (m, 4H).

Step C: (1S)-1-[((3R,4R)-2,5-Dioxo-3,4-dibenzoyloxypyrrolidinyl)-oxycarbonyloxy]-2-methylpropyl 2-methylpropanoate (5)

A 3 L, three necked, round bottom flask fitted with a mechanical stirrer, Teflon-coated temperature probe and an addition funnel was charged with (4) (234 g, 1 mol), (5b) (330 g, 0.95 mol), and 1,2-dichloroethane (2200 mL). The reaction mixture was cooled under a nitrogen atmosphere in an ice water bath to 15° C. To the stirred reaction mixture was added a 39% solution of peracetic acid in dilute acetic acid (500 mL, 2.94 mol) over 2 h, while maintaining the temperature between 15 and 22° C. This temperature was maintained for an additional 12 h during which time a white precipitate was formed. The reaction mixture was further cooled to 3-4° C., the product collected by filtration, and washed with hexane (2×1 L). The product was dried in vacuo, yielding the title compound (5) (128 g, 0.24 mol, 25%). The diastereomeric purity of the product was determined to be >99% d.e. by HPLC using a chiral column. $^1$H NMR ($CDCl_3$, 400 MHz): δ

1.0 (d, 6H), 1.2 (dd, 6H), 2.1 (m, 1H), 2.65 (m, 1H), 6.0 (br. s, 2H), 6.6 (d, 1H), 7.45 (app. t, 4H), 7.65 (app. t, 2H), 8.05 (d, 4H).

In an alternative synthesis of compound (5), a 5 L, three necked, round bottom flask fitted with a mechanical stirrer, Teflon-coated temperature probe and an addition funnel was charged with (4) (350 g, 1.5 mol), (5b) (530 g, 1.5 mol), and dichloromethane (2 L). The reaction mixture was cooled under a nitrogen atmosphere in an ice water bath to 15° C. To the stirred reaction mixture was added a 32% solution of peracetic acid in dilute acetic acid (914 mL, 4.35 mol) over 4 h, while maintaining the temperature between 15° C. and 20° C. The solution was maintained at this temperature for an additional 16 h, then was transferred to a 22 L separatory funnel and the small aqueous layer was removed. The organic phase was diluted with ethyl acetate (2 L) and was washed with water (6×1 L), 0.2M aqueous sodium metabisulfite (2×1 L), and saturated aqueous sodium chloride (2×1 L). The organic phase was dried over anhydrous sodium sulfate and concentrated in vacuo to afford a white solid. This solid was dissolved in ethyl acetate (2 L) at 50° C. and the solution cooled to ambient temperature over 2 h, then further cooled to 0-2° C. for 1 h. The resulting crystalline material was collected on a sintered glass funnel, washed with cold ethyl acetate and dried under vacuum to afford the title compound (5) as a white solid (103 g, 190 mmol, 12.7%), m.p.=138.5-139.5° C. The diastereomeric purity of the product was determined to be ~89% d.e. by HPLC using a chiral column.

Example 6

Synthesis of 4-{[(1S)-Isobutanoyloxyisobutoxy]carbonylamino}-(3R)-(4-chlorophenyl)-butanoic Acid (6)

To a 3 L, three necked, round bottom flask fitted with a mechanical stirrer, temperature probe, and nitrogen inlet was added (5) (75 g, 139 mmol), (R)-baclofen (31.2 g, 146 mmol), THF (1000 mL), and water (100 mL). The suspension was stirred under a nitrogen atmosphere at 18-20° C. for 4 h. The reaction became homogenous in 30 min. The solvent was removed in vacuo and the reaction mixture was diluted with methyl tert-butyl ether (250 mL) and washed with 1N HCl (1×500 mL) and water (2×200 mL). The organic phase was separated and concentrated in vacuo to leave a white solid. The solid was purified by flash chromatography (800 g silica gel; eluting with 20% acetone in hexane) to afford the product (50 g, 125 mmol, 90% yield) as a white solid. Crystallization from an acetone/hexane mixture or an ethyl acetate/heptane mixture afforded the title compound (5) (50 g, 125 mmol, 90% yield) as a white solid. The diastereomeric purity of the product was determined to be >99% d.e. by HPLC using a chiral column. $^1$H NMR (CDCl$_3$, 400 MHz): δ 0.89 (m, 6H), 1.15 (m, 6H), 1.94 (m, 1H), 2.52 (m, 1H), 2.58 (dd, 1H), 2.78 (dd, 1H), 3.28 (m, 2H), 3.49 (m, 1H), 4.68 (t, 1H), 6.48 (d, 1H), 7.10 (d, 2H), 7.24 (d, 2H). MS (ESI) m/z 398.14 (M–H)$^-$.

In an alternative synthesis of compound (6), to a 1 L, round bottom flask fitted with a mechanical stirrer was added (R)-baclofen (40.3 g, 189 mmol), compound (5) (99.3 g, 184 mmol, d.e.=89%), acetone (225 mL), methyl tert-butyl ether (525 mL), and water (75 mL). The suspension was stirred at 20-22° C. for 2.5 h. Analysis of the reaction mixture by LC/MS after 1.5 h indicated that starting material (5) had been completely consumed. The reaction mixture was washed with 2% aqueous HCl (30 mL) and saturated aqueous sodium chloride solution (3×200 mL). The organic phase was dried over anhydrous sodium sulfate, filtered, and concentrated in vacuo to provide an orange oil (160 g). The oil was dissolved in dichloromethane (120 mL), and applied to an 800 g Biotage 75 L silica gel chromatography cartridge in a Biotage Flash 75 Radial Compression Module. The dichloromethane was removed by applying a vacuum to the base of the column for 20 minutes. The desired product was eluted from the column with 14% v/v acetone in hexane (20 L total volume). The eluant was initially collected in 500 mL fractions until the product was observed eluting by TLC, at which point it was collected in 2×4 L fractions, then collected in 400 mL fractions until by-product was observed in the eluant (by TLC). The fractions containing no visible impurities by TLC were combined, concentrated under reduced pressure and dried in vacuo to afford the title compound (6) (70 g, 175 mmol, 95% yield). The chemical purity of the product was determined to be ca. 98.2% AUC (by LC-UV) and the diastereomeric purity determined to be ca. 88.4% d.e. by HPLC using a chiral column. The product was recrystallized by dissolution of the solid in acetone (175 mL) with warming to 53° C. in a water bath, followed by the gradual addition of hexane (1575 mL) over 45 minutes, maintaining the internal temperature between 47 and 52° C. The clear solution was allowed to cool to ambient temperature over 2 h, followed by further cooling to 0-2° C. for 1 h. The product was collected by filtration and washed with cold acetone/hexane (25 mL/225 mL) and dried in a vacuum oven at 45° C. for 24 h, to give the title compound (6) (59.5 g, 149 mmol) as a white crystalline solid. The chemical purity of the product was determined to be ~99.9% AUC (by LC-UV) and the diastereomeric purity determined to be ~98.7% d.e. by HPLC using a chiral column.

Example 7

Synthesis of Sodium 4-{[(1S)-Isobutanoyloxyisobutoxy]carbonylamino}-(3R)-(4-chlorophenyl)-butanoate (7)

The carboxylic acid (6) was converted to the sodium salt by dissolution in MeCN and then addition of aqueous NaHCO$_3$ (1 eq.) with sonication for 15 min. The solvent was removed by lyophilization. Crystallization from either mixtures of acetone/hexane, ethyl acetate/heptane, THF/heptane or 1,2-dimethoxyethane/hexane afforded the title compound (7) as a white crystalline solid. 1H NMR (CD$_3$OD, 400 MHz): δ 0.90 (d, 6H), 1.14 (d, 3H), 1.15 (d, 3H), 1.91 (m, 1H), 2.40 (m, 1H), 2.52 (m, 2H), 3.30 (m, 3H), 6.41 (d, 1H), 7.22 (s, 4H). MS (ESI) m/z 398.08 (M–Na)$^-$.

What is claimed is:

1. A method of treating urinary incontinence in a patient comprising administering to a patient in need of such treatment a therapeutically effective amount of (3R)-4-{[(1S)-2-methyl-1-(2-methylpropanoyloxy)propoxy]carbonylamino}-3-(4-chlorophenyl)butanoic acid or a pharmaceutically acceptable salt thereof.

2. The method of claim 1, wherein the (3R)-4-{[(1S)-2-methyl-1-(2-methylpropanoyloxy)propoxy]carbonylamino}-3-(4-chlorophenyl)butanoic acid is crystalline.

3. The method of claim 1, wherein the (3R)-4-{[(1S)-2-methyl-1-(2-methylpropanoyloxy)propoxy]carbonylamino}-3-(4-chlorophenyl)butanoic acid or pharmaceutically acceptable salt thereof is (3R)-4-{[(1S)-2-methyl-1-(2-methylpropanoyloxy)propoxy]carbonylamino}-3-(4-chlorophenyl)butanoic acid.

4. The method of claim 1, wherein the (3R)-4-{[(1S)-2-methyl-1-(2-methylpropanoyloxy)propoxy]carbonylamino}-3-(4-chlorophenyl)butanoic acid is administered orally.

5. The method of claim 4, wherein the (3R)-4-{[(1S)-2-methyl-1-(2-methylpropanoyloxy)propoxy]carbonylamino}-3-(4-chlorophenyl)butanoic acid is formulated in a sustained release oral dosage form.

6. The method of claim 1, wherein the (3R)-4-{[(1S)-2-methyl-1-(2-methylpropanoyloxy)propoxy]carbonylamino}-3-(4-chlorophenyl)butanoic acid is administered in an amount from about 5 mg-equivalents (R)-baclofen/day to about 100 mg-equivalents (R)-baclofen/day.

7. The method of claim 1, wherein the urinary incontinence is functional incontinence.

8. The method of claim 1, wherein the urinary incontinence is urge incontinence.

9. The method of claim 1, wherein the urinary incontinence is stress incontinence.

10. The method of claim 1, wherein the urinary incontinence is overactive bladder.

11. The method of claim 10, wherein the overactive bladder is characterized by frequency and nocturia.

12. The method of claim 1, wherein the urinary incontinence is mixed incontinence.

13. The method of claim 1, wherein the (3R)-4-{[(1S)-2-methyl-1-(2-methylpropanoyloxy)propoxy]carbonylamino}-3-(4-chlorophenyl)butanoic acid is formulated as a pharmaceutical composition comprising the (3R)-4-{[(1S)-2-methyl-1-(2-methylpropanoyloxy)propoxy]carbonylamino}-3-(4-chlorophenyl)butanoic acid and a pharmaceutically acceptable vehicle.

14. The method of claim 13, wherein the (3R)-4-{[(1S)-2-methyl-1-(2-methylpropanoyloxy)propoxy]carbonylamino}-3-(4-chlorophenyl)butanoic acid is crystalline.

15. The method of claim 13, wherein the pharmaceutical composition is a sustained release oral formulation.

16. The method of claim 13, wherein the pharmaceutical composition is administered in an amount from about 5 mg-equivalents R-baclofen/day to about 100 mg-equivalents R-baclofen/day.

17. The method of claim 1, comprising administering a muscarinic receptor antagonist.

18. The method of claim 17, wherein the muscarinic receptor antagonist is selected from oxybutynin, tolterodine, trospium, solifenacin, and darifenacin.

19. A method of treating urinary incontinence in a patient comprising administering to a patient in need of such treatment a therapeutically effective amount of a pharmaceutical composition comprising (3R)-4-{[(1S)-2-methyl-1-(2-methylpropanoyloxy)propoxy]carbonylamino}-3-(4-chlorophenyl)butanoic acid, or a pharmaceutically acceptable salt thereof, and a pharmaceutically acceptable vehicle.

20. The method of claim 19, wherein the (3R)-4-{[(1S)-2-methyl-1-(2-methylpropanoyloxy)propoxy]carbonylamino}-3-(4-chlorophenyl)butanoic acid is crystalline.

* * * * *